United States Patent [19]

Neier et al.

[11] Patent Number: 4,581,475

[45] Date of Patent: Apr. 8, 1986

[54] PROCESS FOR CONTINUOUSLY PRODUCING ALCOHOLS

[75] Inventors: Wilhelm Neier; Werner Webers; Michael Dettmer, all of Rheinberg, Fed. Rep. of Germany

[73] Assignee: Deutsche Texaco Aktiengesellschaft, Hamburg, Fed. Rep. of Germany

[21] Appl. No.: 652,987

[22] Filed: Sep. 21, 1984

[30] Foreign Application Priority Data

Oct. 8, 1983 [DE] Fed. Rep. of Germany ....... 3336644

[51] Int. Cl.$^4$ ...................... C07C 29/00; C07C 29/86; C07C 31/10; C07C 31/12
[52] U.S. Cl. ..................................... 568/907; 568/918
[58] Field of Search ................................ 568/907, 918

[56] References Cited

U.S. PATENT DOCUMENTS

| | | | |
|---|---|---|---|
| 2,974,175 | 3/1961 | Watts et al. | 568/907 |
| 3,846,088 | 11/1974 | Brown et al. | 568/918 |
| 4,374,286 | 2/1983 | Schmidt | 568/907 |
| 4,384,148 | 5/1983 | Schmidt | 568/907 |
| 4,393,256 | 7/1983 | Schmidt | 568/907 |
| 4,405,822 | 9/1983 | Bezman | 568/907 |

FOREIGN PATENT DOCUMENTS 82447 6/1983 European Pat. Off. ........... 568/918

Primary Examiner—J. E. Evans
Attorney, Agent, or Firm—Robert A. Kulason; James F. Young; James J. O'Loughlin

[57] ABSTRACT

A process for producing a lower aliphatic alcohol by splitting ethers whereby ethers are reacted at an elevated temperature and pressure with an excess of water in the presence of acidic hydration catalysts is disclosed.

7 Claims, 2 Drawing Figures

PROCESS FOR CONTINUOUSLY PRODUCING ALCOHOLS

BACKGROUND OF THE INVENTION

Methods for the preparation of aliphatic alcohols having from 1 to 5 carbon atoms from the corresponding olefins are well known. Broadly, an enriched olefin feedstream is reacted in the presence of an acidic reacting catalyst at an elevated temperature to produce the reaction product containing a saturated aliphatic alcohol. In the direct hydration process, an olefin feedstream and water are contacted with a solid catalyst having acidic reaction sites to produce an aqueous reaction product containing the product alcohol.

During the synthesis of alcohols by acidic hydration of olefins, the corresponding ether is also formed as an undesired by-product. It is known that the formation of ether can be repressed by recycling the ethers distilled off from the alcohols. If the formation of ether is completely suppressed by recycling the ether to the feedstock charged to the reactor, significant disadvantages are encountered. For instance, we have found in test runs that the space/time yield e.g. in the IPA synthesis decreases by this measure by 30% to 50%, depending on the concentration of the propylene feedstock. Moreover, if large amounts of gas are recycled, i.e. if the gas conversion per pass is low, considerable quantities of ether have to be recycled. The additional vaporization of ether in the feedstock results in a higher energy consumption.

An alternative method is the separate splitting of ether by passing the vaporous ether over alumina, cf. Houben-Weyl, Methoden der Organischen Chemie (Methods of Organic Chemistry) VI 3 (1965), 143. However, by the reaction of diisopropyl ether mainly propene and only small amounts of alcohol are obtained. No process for the direct conversion of an aliphatic ether according to the equation $$R-O-R'+H_2O \rightarrow ROH+R'OH \text{ or}$$

$$R-O-R+H_2O \rightarrow 2ROH,$$

wherein R and R' represent alkyl groups with 1 to 5 carbon atoms, is known.

It is the object of the present invention to make available a process allowing the direct and quantitative conversion of an ether into the corresponding alcohol thereby increasing the yield of the alcohol.

DISCLOSURE STATEMENT

U.S. Pat. No. 2,050,445 relates to the production of ethanol by a continuous process using aqueous phosphoric acid as a catalyst. It is reported that the further formation of ether can be repressed by recycling diethyl ether together with the recycled gas.

Canadian Pat. No. 867,797 discloses the recycling of di-isopropyl ether to the recycled gas of the isopropyl alcohol synthesis process.

DE-OS No. 27 59 237 also discloses recycling of the by-products to the feedstock being fed to the reactor.

DE-OS No. 28 02 199 (EP 3305) discloses the preparation of pure isobutene from $C_4$-hydrocarbon streams using $C_3$, $C_4$ alcohols, the respective tertiary butyl ether being formed in each case as an intermediate.

U.S. Pat. No. 2,519,061 discloses a process for the hydration of ethers using superatmospheric pressure.

U.S. Pat. No. 4,405,822 discloses the hydration of diisopropyl ether.

SUMMARY OF THE INVENTION

According to the instant invention, the problem is solved by a process characterized by contacting ether of the general formula $$R-O-R_1,$$

wherein R and $R_1$ represent alkyl groups having 1 to 5 carbon atoms, with an excess of water at a temperature of 100° to 180° C. and a pressure of 10 to 100 bar in the presence of an acidic hydration catalyst, recycling the fluid ether phase, separating the aqueous alcohol phase from the reactor, and working up this phase to recover the alcohol therefrom.

DETAILED DESCRIPTION OF THE INVENTION

According to a preferred embodiment of the process of the invention, the alcohol contained in the fluid ether phase is extracted therefrom, particularly with water, prior to recycling this ether phase to the splitting reactor.

The process of the invention allows the direct and quantitative conversion of an ether into alcohols. Essentially, only the aqueous phase containing the formed alcohol is withdrawn from the process. In a subsequent process step the alcohol (besides a small amount of dissolved ether) can be distilled off from this alcoholic solution.

When performing the process of the invention, it is surprising that practically no olefin is obtained. No gas is removed from the reaction system. During the splitting of diisopropyl ether only 2 to 3% propylene are dissolved in the organic phase with which the propylene is in equilibrium. These amounts are not separated but are continuously recycled with the ether stream to the reactor.

The figures attached hereto illustrate embodiments of the process according to the invention.

Figure 1:
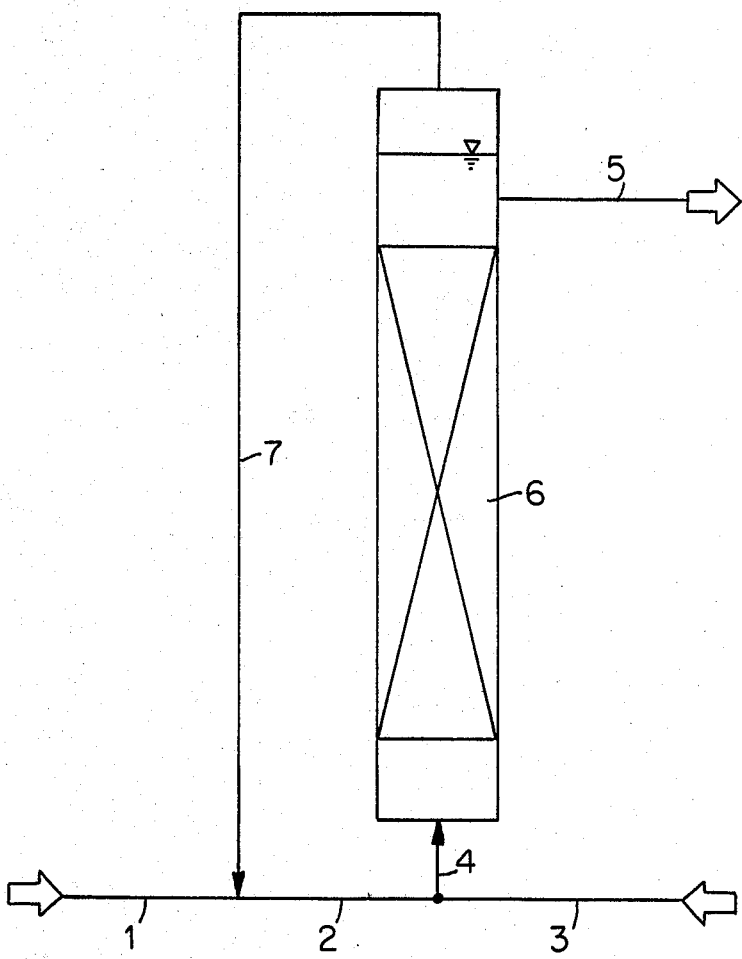
FIG. 1 shows the possible design of the reactor as a sump reactor.

According to FIG. 1, ether from line 1 and water from line 3 are continuously charged together through line 4 into a tube reactor (6) packed with ion exchange resin. The ether is hydrolyzed by an acid-catalyzed multiphase reaction at elevated pressure and temperature. The formed alcohol and the two educts spread in two unmixable liquid phases, an alcohol/water phase and an ether/alcohol phase. For this process it is advantageous that the alcohol is more readily soluble in the aqueous phase than the ether. Hence, after the phases have separated, the desired reaction product and a small portion of ether with an excess of water can be drained through line 5. Unreacted ether and small amounts of olefin, if any, which separate at the reactor head to form the upper phase, are recharged through line 7 to reactor 6 without intermediate treatment. To split a great amount of ether (>90%) and to insure that the two phases are thoroughly mixed, the lighter phase (ether/alcohol) separating at the reactor head is recycled at a relatively high velocity to the reactor sump. Thus, the ether feed is completely converted into alcohol (with the exception of the ether that is withdrawn with the product water and that can be recycled after distillation), because the recycled olefins, too, can be hydrated under reaction conditions to form alcohols. The conversion is 90 to 93%, not including the recycling of ether phased out with the alcohol (see example 1). A nearly complete conversion is attained if the recycling is included.

Figure 2:
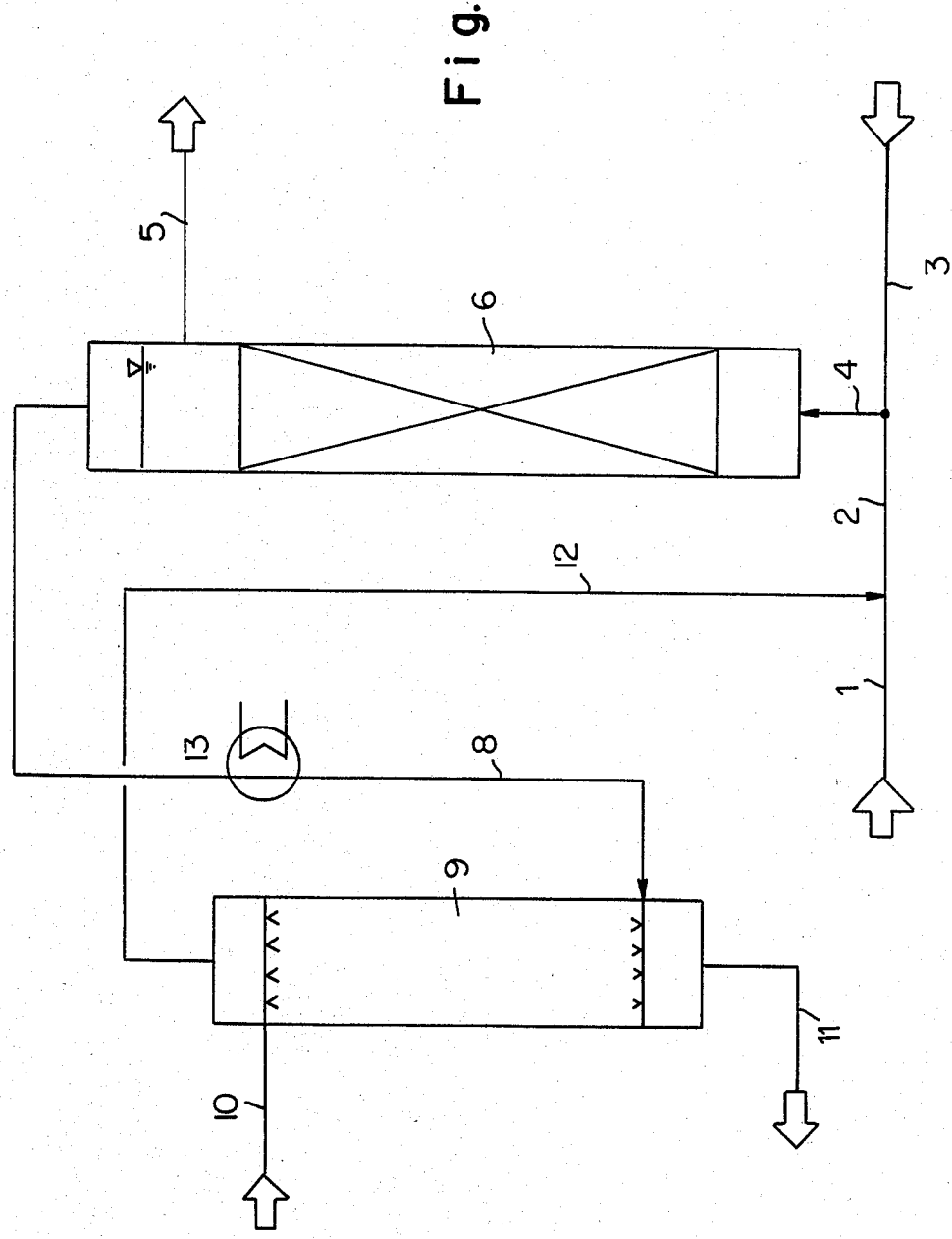
FIG. 2 shows a process design including an extractor.

According to FIG. 2, the recycle stream is charged through line 8 to the extractor (9) where at a lower temperature, particularly at 80° to 100° C., the relatively big portion of alcohol contained in the recycle stream is washed out with water. The alcohol-free recycle stream is then reheated in line 12 and recycled to the splitting reactor.

The catalyst used for the splitting of ether is a liquid, particularly solid, acidic catalyst normally used for the hydration of olefins. Temperature-stable ion exchange resins of the sulfonic acid type are particularly preferred.

The temperature in the splitting reactor ranges between 100° and 180° C. If organic ion exchange resins are used, the upper temperature limit is determined by the temperature resistance of the catalyst. The pressure ranges between 10 and 100 bar. The process for splitting ether is largely independent of pressure. The pressure is mainly applied to keep the two phases in a liquid condition.

The splitting of ether according to the invention requires an ether/water mole ratio of above 1 mole of ether to 3 moles of water. The mole ratio is particularly above 1 mole of ether to 10 moles of water, and a ratio of about 1 mole of ether to 50 to 100 moles of water is particularly preferred.

The space/time yield is 1 to 2 moles of alcohol/1 cat.h, and if the recycle stream is freed from alcohol by extraction with water, it is even 3.5 moles/1 cat.h and more.

In the splitting of DIPE the alcohol content in the aqueous phase of stream 5 is up to 10 to 15% wt. and higher, and the ether content in the aqueous phase is at most 1% wt., but normally less.

The following examples illustrate the practice of this invention with the aid of FIGS. 1 and 2. The amounts stated as percent mean percent by weight.

EXAMPLE 1

254 grams/h of diisopropyl ether (DIPE) were charged through line 1 and 2225 grams/h of demineralized water were charged through line 3 into reactor 6 of the unit according to FIG. 1 which has an internal diameter of 26 mm and a length of 5 meters and is packed with 2.5 liters of the strongly acidic ion exchange resin Amberlite 252 used as a catalyst. 23 l/h of the upper organic phase formed in the reactor composed of 72% unsplit ether, 20% isopropyl alcohol, 5% water, and 3% propylene were recycled together with the ether feed through line 7 to the sump of reactor 6. Using a heating jacket, the reaction temperature in the reactor was adjusted at 155° C. The pressure in the reactor was maintained at 50 bar.

From reactor 6 2455 g/h of an aqueous liquid phase containing 11.0% isopropyl alcohol and 1% diisopropyl ether were drained through line 5. 108 grams of isopropyl alcohol (1.8 moles) were formed per liter of catalyst per hour. No gaseous phase was obtained.

EXAMPLE 2

The run described in Example 1 was repeated, the difference being that the reaction pressure was lowered to 25 bar. The same results as in Example 1 were obtained.

EXAMPLE 3

The run described in Example 1 was repeated in the unit depicted in FIG. 2, the difference being that the upper organic phase was cooled to 100° C. by means of heat exchanger 13 and then was charged through line 8 to extractor 9 in order to remove part of the isopropyl alcohol from the recycle ether. The ether feed charged through line 1 was increased to 450 g/h, the water feed was raised to 3292 g/h, and 2058 g/h of water were charged through line 10 to extractor 9. Then 3440 g of a 5.9% isopropyl alcohol aqueous phase containing 0.5% ether were obtained from line 5. 2361 g/h of another aqueous isopropyl alcohol phase were drained through line 11. The isopropyl alcohol content in this phase was 11.9% on an average, the isopropyl ether content was 0.9%.

194 g of isopropyl alcohol (3.2 moles) were obtained per liter of catalyst per hour.

EXAMPLE 4

Example 3 was repeated, the difference being that 495 g of disec. butyl ether (DSBE) were fed through line 1 and 3398 g of demineralized water were fed through line 3. Additionally, 6966 g of water were charged to extractor 9. 3484 g/h of a 3.2% sec. butyl alcohol (SBA) containing 0.04% DSBE were obtained from line 5. 7400 g/h of a 6% sec. butyl alcohol containing 0.06% DSBE were obtained from line 11. The stream recycled through line 12 to reactor 6 (23 l/h) contained about 88% DSBE, 2 to 3% butenes, approximately 9% SBA, and a small portion of water.

222 g of SBA (3.0 moles) were obtained per liter of catalyst per hour.

We claim:

1. In a process for producing a lower aliphatic alcohol having from 1 to 5 carbon atoms which comprises reacting an ether represented by the formula: R—O—$R_1$ in which R and $R_1$ each represent an alkyl radical having from 1 to 5 carbon atoms at an elevated temperature and pressure in the presence of an acidic catalyst, the improvement which comprises reacting said ether with an excess of water at a temperature of 100°–180° C. and a pressure of 10 to 100 bar in the presence of an acidic hydration catalyst to produce a fluid ether phase comprising ether and alcohol and an aqueous phase comprising water and alcohol, recycling said fluid ether phase to said reactor, withdrawing said aqueous phase containing product alcohol from said reactor and recovering said aliphatic alcohol from said aqueous phase.

2. A process according to claim 1 in which the aliphatic alcohol contained in said fluid ether phase is extracted with water prior to recycling said ether phase to said reactor.

3. A process according to claim 1 in which the mole ratio of said water to said ether ranges from about 3 to 100 moles of water per mole of said ether.

4. A process according to claim 1 in which the mole ratio of said water to said ether is about 10 to 1.

5. A process according to claim 1 in which the mole ratio of said water to said ether is about 3 to 1.

6. A process according to claim 1 in which said ether is diisopropyl ether.

7. A process according to claim 1 in which said ether is di-sec. butyl ether.

* * * * *